United States Patent
Duggan et al.

(10) Patent No.: US 7,388,463 B2
(45) Date of Patent: Jun. 17, 2008

(54) ELECTROMAGNETIC COIL ASSEMBLY EMPLOYING SPOOL-SPINDLE

(75) Inventors: John Duggan, Tonawanda, NY (US); Norbert W. Frenz, Jr., Williamsville, NY (US)

(73) Assignee: Infusion Systems, LLC, Sylmar, CA (US)

( * ) Notice: Subject to any disclaimer, the term of this patent is extended or adjusted under 35 U.S.C. 154(b) by 179 days.

(21) Appl. No.: 11/048,149

(22) Filed: Feb. 1, 2005

(65) Prior Publication Data

US 2006/0033600 A1    Feb. 16, 2006

Related U.S. Application Data

(60) Provisional application No. 60/601,837, filed on Aug. 16, 2004.

(51) Int. Cl.
  *H01F 27/30* (2006.01)
(52) U.S. Cl. ..................... 336/208; 417/44.1
(58) Field of Classification Search ................. 336/208
  See application file for complete search history.

(56) References Cited

U.S. PATENT DOCUMENTS

| | | | |
|---|---|---|---|
| 4,290,040 A | 9/1981 | Feightner et al. | |
| 4,379,681 A | 4/1983 | Goudy, Jr. | |
| 5,797,733 A * | 8/1998 | Falk et al. | 417/416 |
| 6,310,533 B2 * | 10/2001 | Coulombier | 336/90 |
| 6,595,756 B2 * | 7/2003 | Gray et al. | 417/44.1 |
| 6,641,378 B2 | 11/2003 | Davis et al. | |
| 2003/0050624 A1 | 3/2003 | Gray et al. | |
| 2003/0050625 A1 | 3/2003 | Lorenzen et al. | |
| 2003/0130647 A1 | 7/2003 | Gray et al. | |
| 2003/0135160 A1 | 7/2003 | Gray et al. | |

* cited by examiner

*Primary Examiner*—Elvin Enad
*Assistant Examiner*—Joselito Baisa
(74) *Attorney, Agent, or Firm*—Henricks, Slavin & Holmes LLP

(57) ABSTRACT

An electromagnetic coil assembly comprising a spool-spindle and a case. The spool-spindle comprises a spindle portion and a larger included portion. The spindle portion has a conductor wound thereon. The larger included portion has opening for receiving the conductor. The case has a first case end and a second case end, with an opening extending through the case. A first internal surrounding surface extends from the second case end and a second surrounding internal surface having a smaller diameter extends from the first case end. The first internal surrounding surface meets the second internal surrounding surface at an annular internal wall. The spool-spindle is positioned in the case until the larger include portion abuts against the annular internal wall, and the case and spool-spindle are joined.

11 Claims, 5 Drawing Sheets

ELECTROMAGNETIC COIL ASSEMBLY EMPLOYING SPOOL-SPINDLE

BENEFIT CLAIM OF PRIOR APPLICATION

This application claims the benefit of U.S. Provisional Application No. 60/601,837, filed Aug. 16, 2004, to Duggan et al., for an Electromagnetic Coil Employing Spool-Spindle.

FIELD OF THE INVENTION

The present invention relates to an electromagnetic coil assembly comprising a spool-spindle with wound conductor used for generating an electromagnetic field.

BACKGROUND

An electromagnetic coil assembly typically includes a case. Internal to the case is a spindle with a conductor or wire wound around the spindle. The conductor is typically helically wound around the spindle. One example of use of electromagnetic coil assemblies such as these is in combination with drug pumps and drug delivery control valves. FIG. 1 shows a sectional view of a prior art electromagnetic coil assembly used in such devices, and reference may be made to U.S. Pat. No. 6,264,439 for a more detailed description thereof.

Briefly, the prior art electromagnetic coil assembly shown in FIG. 1 has a case 20, and internal to the case is a spindle 12. The case 20 is typically a manufactured part made by a turning process, and the case defines an opening that is symmetric about an axis of revolution. The spindle 12 is also typically a turned part that is symmetric about its principal axis and is of ferromagnetic material. The wire coil or conductor winding 14 is helically wound around a central portion of the spindle, and when current passes through the coil an electromagnetic field is generated. The prior art electromagnetic coil assembly also includes a washer 16 pressed onto one end of the spindle and a locater or spacer 18 pressed onto the other end of the spindle. The washer and locater are press fit onto opposite ends of the spindle and held thereon by a friction fit. Fixturing is employed to hold all the components in place while the case is being filled with a potting compound or epoxy 24, and while the epoxy cures. The epoxy is added in two separate phases or steps. The case is then fitted to an electromagnetic device 26.

In the prior art, the combination of the washer and the locater serve to center the spindle within the case. The washer, however, does not fully constrain the spindle, and the spindle can therefore travel, along with the associated washer, in the direction of its principal axis. When the coil case is filled with potting epoxy, the spindle is locked in position. Furthermore, if there is no locator, the free end of the spindle opposite the washer additionally must be held concentric with the case and constrained in the axial direction until the potting compound has cured. Fixturing establishes the distance from the washer end of the spindle to the plane established by the washer end of the case.

What is needed is an improved electromagnetic coil assembly and method that does not require washers, provides for improved stability of components, decreases production time, and reduces fixturing requirements.

SUMMARY

The electromagnetic coil assembly of the present invention comprises a spool-spindle that is joined to a case. The spool-spindle comprises a spindle portion and a larger included portion that is joined to or integral with the spindle portion. The spindle portion and larger included portion is of ferromagnetic or conductive material and has a coil wound thereon. The larger included portion also defines an opening through which a conductor(s) of the coil can extend and through which epoxy can be introduced.

More specifically, the spool-spindle comprises a first end and an opposed second end, and the larger included portion is positioned between the first end and the second end. Also, the larger included portion comprises a first spool surface, an opposed second spool surface, and a surrounding spool surface that extends between the first spool surface and the second spool surface. A chamfer can be formed in the larger included portion between the surrounding spool surface and the second spool surface.

The case to which the spool-spindle is joined comprises a first case end and a second case end, with a cylindrical shaped outer surface extending between the first case end and second case end. An open region is defined in the case extending from the first case end to the second case end. The case further comprises a first internal surrounding surface extending from the second case end in a direction toward the first case end, and a second internal surrounding surface extending from the first case end in a direction toward the second case end. The first internal surrounding surface has a greater diameter than the second internal surrounding surface, and the first internal surrounding surface and the second internal surrounding surface meet at an annular internal wall. The annular internal wall provides a shoulder or stop for the larger included portion of the spool-spindle to abut against when it is positioned in the case.

The electromagnetic coil assembly is made by providing the above-described case and spool-spindle, winding a conductor around the spindle portion of the spool-spindle, moving the spool-spindle into the case until the larger included portion abuts against the annular internal wall, and joining the spool-spindle and the case together. The joining can be by friction fit, welding, crimping, and the like. Electrical potting epoxy is introduced into the assembly to fill the spaces between the spool-spindle, coil, and case.

Some of the advantages of an electromagnetic coil assembly employing the spool-spindle are that fewer components need to be manufactured, assembly steps are eliminated, and dimensional accuracy of the final assembly is easier to control because there are fewer component interface locations.

BRIEF DESCRIPTION OF THE FIGURES

At the outset, it should be noted that like reference numbers are intended to identify the same structure, portions, or surfaces consistently throughout the figures.

DETAILED DESCRIPTION

Figure 1:
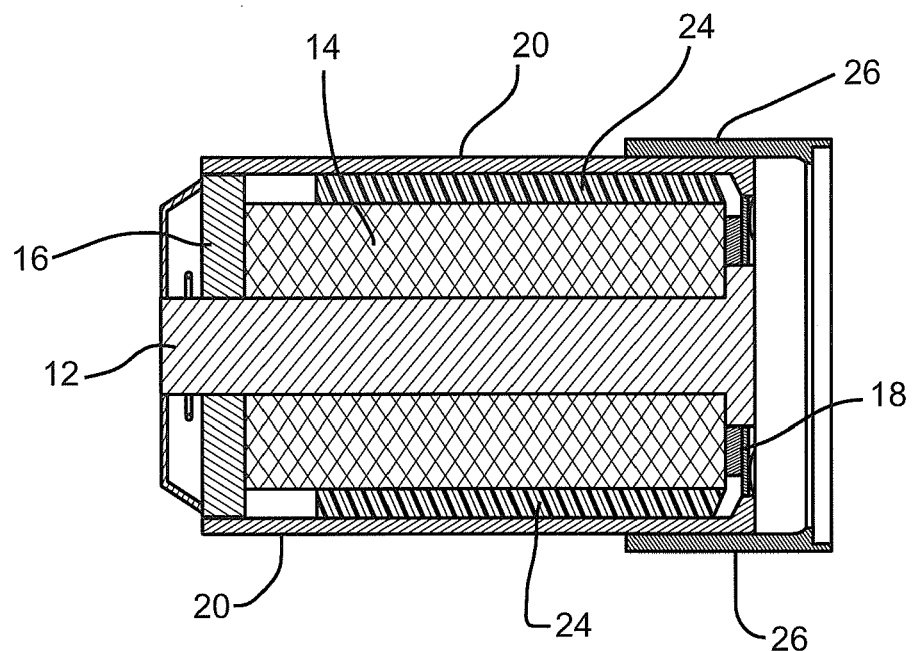
FIG. 1 is a sectional view of a prior art electromagnetic coil assembly having an outer case, internal washer, a spindle, and a locator held together with epoxy.
Figure 2:
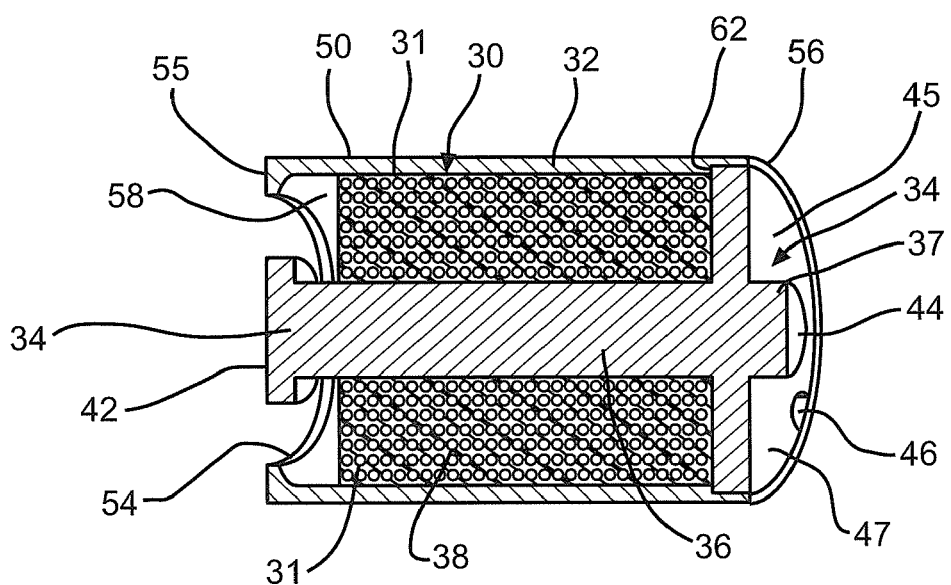
FIG. 2 is a sectional perspective view of an electromagnetic coil assembly of the invention comprising a spool-spindle and a case with a conductor winding and epoxy.
Figure 3:
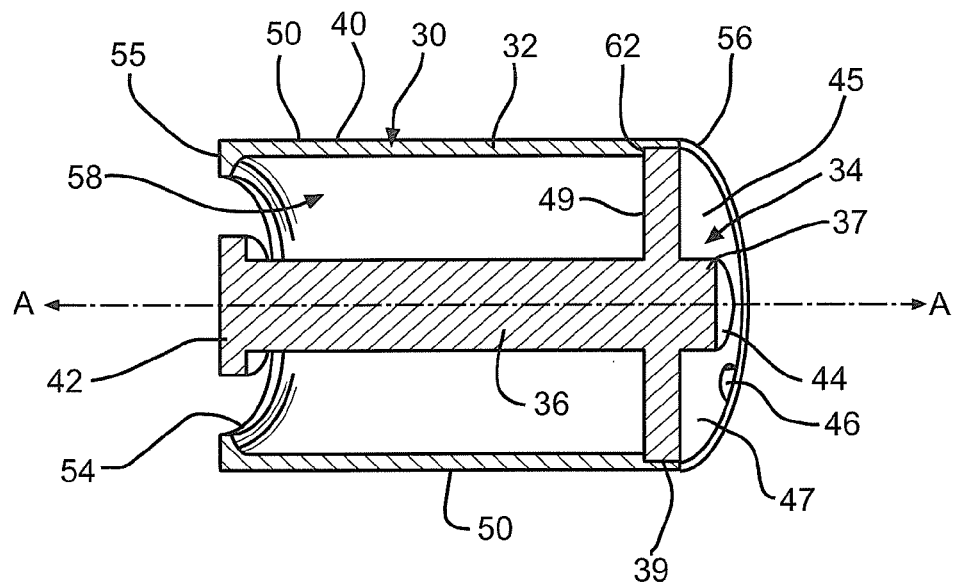
FIG. 3 is a sectional perspective view of the spool-spindle and case without conductor and epoxy.

FIG. 2 is a sectional view of the electromagnetic coil assembly 30 of the invention. The electromagnetic coil assembly 30 comprises a case 32 and a spool-spindle 34. As shown, the spool-spindle 34 is centrally positioned inside the case 32. The electromagnetic coil assembly 30 further comprises a conductor winding 31 that is wound around the spool-spindle 34 to form a coil for generating an electromagnetic field.

Figure 6:
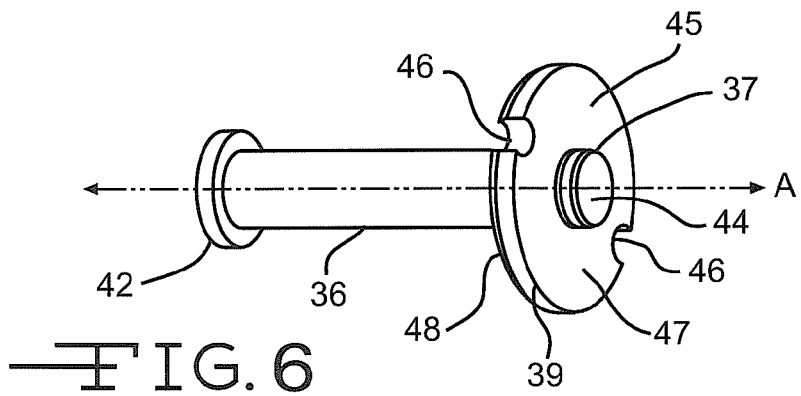
FIG. 6 is a perspective view of the spool-spindle.
Figure 7:
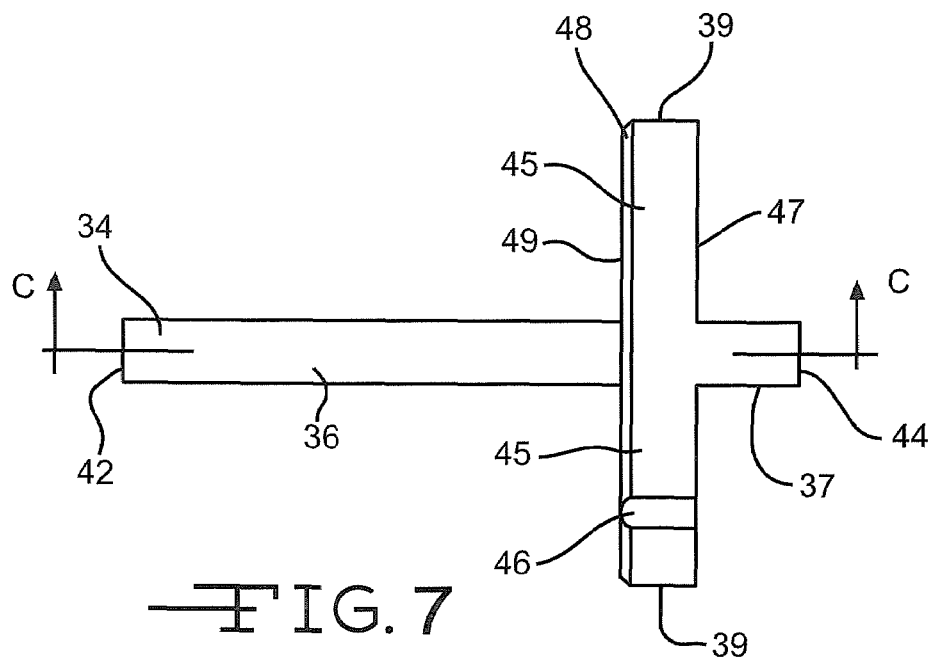
FIG. 7 is a front elevational view of the spool-spindle.
Figure 8:
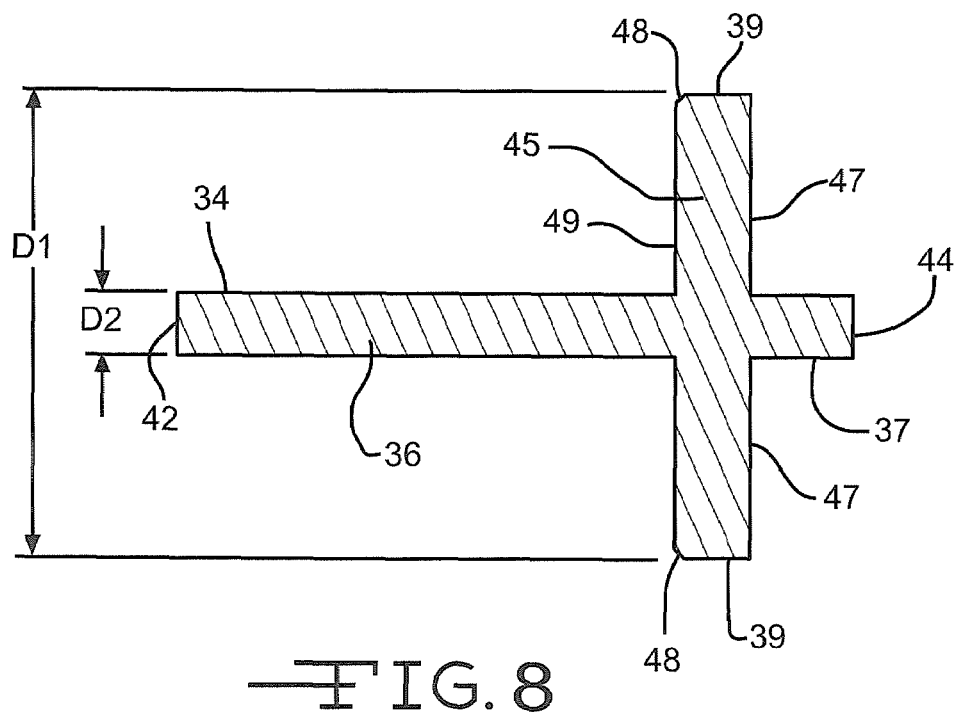
FIG. 8 is a sectional view of the of the spool-spindle taken along cut line C-C in FIG. 7.

As shown in FIGS. 2-4, 6-8, the spool-spindle 34 has a first axial end 42 and an opposed second axial end 44. The spool-spindle 34 includes a spindle portion 36 that extends from the first end 42 to a larger included portion 45, and the spindle portion 36 and larger included portion 45 are joined to one another. In one of the preferred embodiments, the larger included portion 45 is formed integral with the spindle portion 36, as shown in FIGS. 7 and 8, for example being machine turned from a single piece of material. FIG. 8 is a sectional view of the spool-spindle 34 taken along cut line C-C of FIG. 7. The larger included portion 45 has a larger diameter designated D1 in FIG. 8, and the spindle portion 36 has a smaller spindle diameter designated D2 in FIG. 8, as compared to the larger diameter designated D1. As shown, the spindle portion 36 in is in the form of a rod or shaft, and the larger included portion 45 is in the form of a disc.

The spool-spindle 34 further comprises an extension portion 37, as shown in FIGS. 2-4, and 6-8. The extension portion 37 extends axially from the second end 44 of the spool-spindle 34 to the larger included portion 45, and is joined to the larger included portion 45. In one of the preferred embodiments the extension portion 37 is formed integral with the larger included portion 45. Also, the diameter of the extension portion 37 can be the same as the diameter D2 of the spindle portion 36.

As shown in FIGS. 7 and 8, the larger included portion 45 defines a first spool surface 47 and an opposed second spool surface 49. In one of the preferred embodiments, a lead-in chamfer 48 is formed in the larger included portion 45. The lead-in chamfer 48 is used for facilitating the assembly of the spool-spindle 34 in case 32. A surrounding or peripheral spool surface 39 extends around the larger included portion 45. In particular, and as shown in FIG. 8, the surrounding spool surface 39 extends between the lead-in chamfer 48 and the first spool surface 47. The first spool surface 47 extends from the surrounding spool surface 39 to the extension portion 37, and the second spool surface 49 extends from the lead-in chamfer 48 to the spindle portion 36. It is noted that in other embodiments, the lead-in chamfer 48 can be eliminated.

Also, the larger included portion 45 defines spool openings 46 used for receiving a conductor(s) 31 and/or used for allowing potting compound or epoxy 38 to be introduced into the case 32. As shown in FIG. 6, the longitudinal axis of the spool-spindle 34 is designated A.

Figure 4:
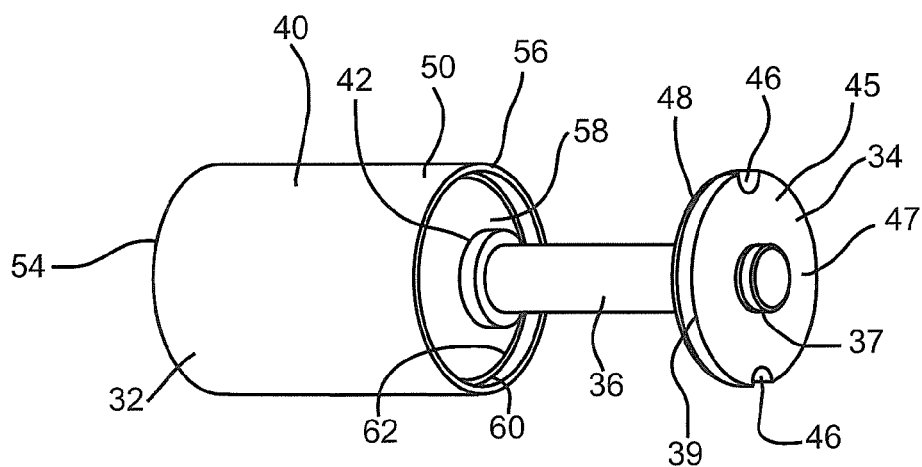
FIG. 4 is a perspective view showing the spool-spindle aligned with the case.
Figure 5:
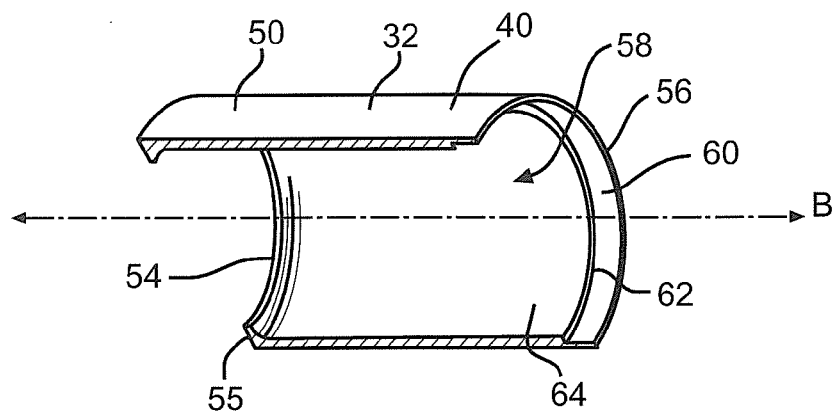
FIG. 5 is sectional perspective view of the case.

The above-described spool-spindle 34 is sized to be positioned inside the case 32. The case 32 is a hollow cylindrical-shaped body 40 as shown in FIG. 4. As shown in FIG. 5, the case 32 has an outer surface 50, a first case end 54, an opposed second case end 56, and defines an open region 58, as shown in FIGS. 4 and 5. Additionally, at the first case end 54 the case 32 has an annular formation 55 that extends into the case open region 58. The case 32 has a longitudinal axis designed B in FIG. 5 that extends through the open region 58.

Additionally, the case 32 has a first internal surrounding surface 60 having a first diameter extending from the second case end 56. The first internal surrounding surface 60 extends toward the first case end 54, until it meets an annular internal wall 62. At the annular internal wall 62 the first internal surrounding surface 60 meets a second internal surrounding surface 64. The second internal surround surface 64 has a diameter less than the diameter of the first internal surrounding surface 60. The annular internal wall 62 defines a shoulder which serves as a stop for the spool-spindle 34, as will be described presently.

To assemble the electromagnetic coil assembly 30, the conductor 31 is wound around the spindle portion 36 of the spool-spindle 34. Then, the case 32 and spool-spindle 34 are axially aligned, such that the longitudinal axis designated A of the spool-spindle 34 and the longitudinal axis designated B of the case 32 are coincident. This arrangement is shown in FIG. 4. Then, the first end 42 of the spool-spindle 34 is moved through the open region 58. It is noted that in order for the spool-spindle 34 to be moved into the case 32, the diameters of the spindle portion 36 and the larger included portion 45 are less than the diameter of the first internal surrounding surface 60 of case 32.

As the spool-spindle 34 continues to be moved longitudinally into the case 32, the lead-in chamfer 48 formed in the larger included portion 45 contacts the annular internal wall 62. As movement continues, the larger included portion 45 seats against the annular internal wall or shoulder 62. Movement of the spool-spindle 34 into the case 32 stops, because the diameter D1 of the larger included portion 45 is greater than the diameter of the second internal surrounding surface 64. Thus, the internal wall 62 acts as a stop, and controls the distance the spool-spindle 34 can be inserted into the case 32.

By virtue of the relative dimensions of portion 45 and the first internal surrounding surface 60, the spool-spindle 34 and case 32 are joined to one another by a press fit or an interference fit. In other embodiments, the spool-spindle 34 and case 32 may be joined by welding, pinning, crimping, and mechanical fasteners. In another embodiment, the first internal surrounding surface 60 of the case 32 may be provided with an internal thread, and the surrounding spool surface 39 provided with an external thread, so that the case 32 and spool-spindle 34 can be threaded together. This threading may be reversed, such that the first internal surrounding surface 60 has an external thread, and the surrounding spool surface 39 has an internal thread.

After assembly, a first plane passes through the first case end 54 surface, such that the first plane is substantially perpendicular to the longitudinal axis of the case 32. The annular internal wall 62 and larger included portion 45 interface establishes the linear distance that the first end 42 of the spool-spindle 34 is spaced from the first plane defined above. The annular internal wall 62 and larger included portion 45 interface also establishes the concentric alignment of the first end 42 of the spool-spindle 34 within the case 32. As one of the advantages of the invention, the alignment within the case 32 is accomplished without washers. For further mechanical stability, in one of the preferred embodiments, the spool opening(s) 46 allows potting epoxy 38 to be introduced into the case 32. This enables potting compound 38 to fill spaces or voids defined between the spool-spindle 34 and the conductors 31, between the conductors 31 and the case 32, and between the individual conductors 31, as shown in FIG. 2. Upon curing, the potting compound 38 robustly joins the internal components of the electromagnetic coil assembly 30 and fixes them in place.

The case 32 and the spool-spindle 34 can be made of magnetically conductive materials. Also, the spool-spindle 34 can be made with a lathe machine (not shown). Lathe machines and the use of lathe machines to make turned parts and components are well known to those having ordinary skill in the art.

Figure 9:
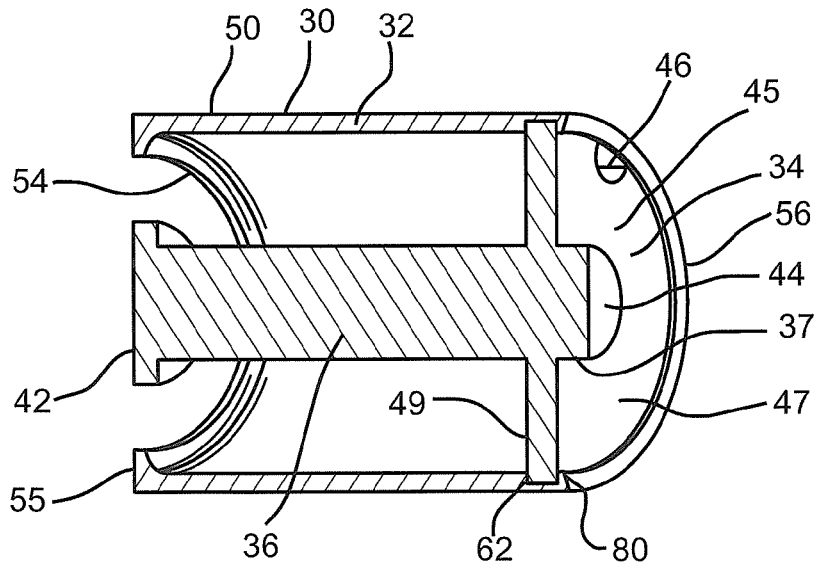
FIG. 9 is a sectional perspective view of another embodiment of a case for receiving the spool-spindle.

As noted above, in another embodiment the spool-spindle 34 may be joined to the case 32 by crimping, and this is shown in FIG. 9. For this purpose, an annular internal lip 80 is provided on casing internal surface 60 near end face 56. The spool spindle 34 is moved into the case 32 in the above-described manner and the lip 80 that surrounds the second case end 56 is crimped as shown in FIG. 9. This joins the spool-spindle 34 and the case 32 as shown in FIG. 9. Crimping increases the degree to which the case 32 and the spool-spindle 34 are joined to one another. As a result, less reliance needs to be placed on the potting epoxy 38 that is also used to join the spool-spindle 34 to the case 32.

In other embodiments, the annular internal wall or shoulder 62 may be eliminated if a fixture (not shown) is used to hold the case 32 and spool-spindle 34 together so that they can be joined together with a weld. In another embodiment, the annular internal wall 62 is eliminated, and fixturing may be employed as well as a locator to fix the location or position of the spool-spindle 34 relative to the case for the process that introduces the means for fastening, such as epoxy 38. The locator may then be removed or remain part of the coil assembly.

In another embodiment a step or shoulder may be machined into the larger included portion 45. Then a portion of the peripheral surface 39 of portion 45 may be received in the open region 58 in the second end 56 of the case 32, but the remainder of the peripheral surface 39 of the larger included portion 45 cannot be received in the open region 58 in the case, due to engagement between the step or shoulder of portion 45 and the annular end surface 56 of the case 32. In such an embodiment, the annular internal wall 62 may or may not be present, because the introduction of the spool-spindle 34 into the case 32 is controlled by the shoulder formed in the larger included portion 45.

The electromagnetic coil assembly 30 employing the above-described spool-spindle 34 has a number of advantages. Some of the advantages are that fewer components need to be manufactured, assembly steps are eliminated, fixturing is eliminated, and dimensional accuracy of the final assembly is easier to control because there are fewer component interface locations. More advantages include the elimination of the washer component from the manufacture and assembly process, optional use of the locater component, the immediate constraining of the spool-spindle 34 upon its insertion into the case 32, and elimination of the washer-spindle interface. Another advantage is that the positions of the spool-spindle 34 and case 32 are easier to control via the dimensions and tolerances used to manufacture the spool-spindle 34 and case 32. In addition, another possible advantage is that the continuity of the magnetic lines of force may be improved by the structure of the spool-spindle thereby possibly improving the performance of the electromagnetic coil.

Figure 10:
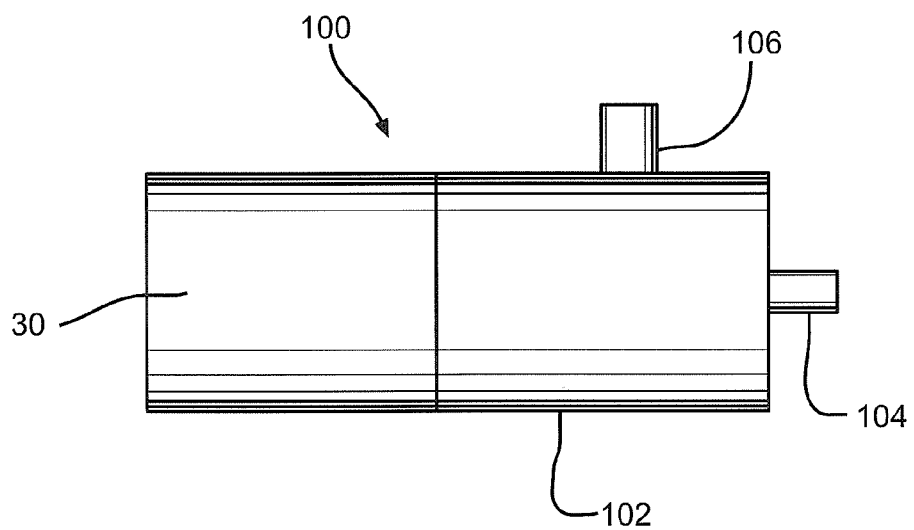
FIG. 10 is a diagrammatic view illustrating the electromagnetic coil assembly of the invention in a low power electromagnetic pump.

FIG. 10 shows the electromagnetic coil assembly 30 in a low power electromagnetic pump 100 which, for example, can be used in implantable drug delivery systems. In the arrangement shown, coil assembly 30 is axially adjacent the pump housing 102 which contains an armature/plunger (not shown) which is magnetically influenced by coil assembly 30 to pump fluid from an inlet 104 connected to a supply reservoir (not shown) to an outlet 106 to a point of use for the fluid. Pulsed operation of coil assembly 30 by an appropriate electrical circuit (not shown), typically battery-operated, causes reciprocating operation of the pump armature/plunger which is typically spring biased. For a more detailed description of such an electromagnetic pump, reference may be made to the previously mentioned U.S. Pat. No. 6,264,439 issued Jul. 24, 2001, the disclosure of which is hereby incorporated by reference.

It will be appreciated by those skilled in the art that while the invention for electromagnetic coil assembly employing a spool-spindle has been described above in connection with particular embodiments and examples, the invention is not necessarily so limited and other embodiments, examples, uses, and modifications and departures from the embodiments, examples, and uses may be made without departing from the invention. All of these alternative embodiments are intended to be within the scope and spirit of the this invention.

What is claimed is:

1. An electromagnetic coil assembly comprising:
    a) a case including a first case end and a second case end, and a first internal surrounding surface and a second internal surrounding surface that meet at an annular internal wall;
    b) a spool-spindle including a spindle portion and a larger included portion that are joined to one another, the larger included portion being joined directly to the longitudinally extending inner surface of the case and having a diameter that is greater than a diameter of the spindle portion; and
    c) a coil located on the spool-spindle.

2. The assembly according to claim 1 wherein the first internal surrounding surface extends from the second case end and the second internal surrounding surface extends from the first case end.

3. The assembly according to claim 2 wherein a diameter of the first surrounding wall is greater than a diameter of the second surrounding wall.

4. An electromagnetic coil assembly comprising:
    a case defining a first case end and a second case end and including a first longitudinally extending internal surrounding surface and a second longitudinally extending internal surrounding surface, the first longitudinally extending internal surrounding surface and the second longitudinally extending internal surrounding surface meeting at an annular internal wall;
    a spool-spindle including a spindle portion and a larger included portion, the larger included portion being joined to the spindle portion and to the case and having a diameter that is greater than the diameter of the spindle portion, less than the diameter of the first longitudinally extending internal surrounding surface, and greater than the inner diameter of the annular internal wall such that when the spool-spindle is positioned in the case the larger included portion abuts against the annular internal wall; and
    a coil located on the spool-spindle.

5. The assembly according to claim 4 wherein the spool-spindle is joined to the case by welding or friction fit.

6. The assembly according to claim 4 wherein the spool-spindle is joined to the case by crimping the second case end around the larger included portion to lock the spool-spindle in place.

7. The assembly according to claim 4 wherein the case further comprises a formed lip at the second end of the case and the formed lip is for holding the spool-spindle in the case.

8. A method of making an electromagnetic coil assembly comprising:

provided a case including a first case end and a second case end, and a first internal surrounding surface that extends from the second case end and a second internal surrounding surface that extends from the first case end, the first internal surrounding surface having an inner diameter greater than the inner diameter of the second internal surrounding surface;

providing a spool-spindle;

providing a coil on the spool-spindle;

inserting the spool-spindle in the case;

centering the spool-spindle relative to the case with the integral internal centering structure of the case; and joining the spool-spindle directly to the case.

9. The method according to claim 8 further comprising forming the spool-spindle with a larger included portion and a spindle portion.

10. The method according to claim 8 further comprising providing the case with an annular internal wall where the first internal surrounding surface and second internal surrounding surface meet.

11. The method according to claim 10 wherein the spool-spindle comprises a larger included portion and a spindle portion and inserting the spool-spindle into the case until the larger included portion abuts against the annular internal wall.

* * * * *